(12) United States Patent
Haran

(10) Patent No.: US 10,736,281 B2
(45) Date of Patent: *Aug. 11, 2020

(54) SOIL SENSOR ASSEMBLY

(71) Applicant: CropX Technologies, Ltd., Herzliya (IL)

(72) Inventor: Yossi Haran, Modi'in-Macabim-Reut (IL)

(73) Assignee: CropX Technologies, Ltd., Herzliya (IL)

(*) Notice: Subject to any disclaimer, the term of this patent is extended or adjusted under 35 U.S.C. 154(b) by 0 days.

This patent is subject to a terminal disclaimer.

(21) Appl. No.: 16/514,116

(22) Filed: Jul. 17, 2019

(65) Prior Publication Data

US 2020/0000050 A1 Jan. 2, 2020

Related U.S. Application Data

(63) Continuation of application No. 15/781,349, filed as application No. PCT/IL2016/000022 on Dec. 1, 2016.
(Continued)

(51) Int. Cl.
*G01R 27/26* (2006.01)
*A01G 25/16* (2006.01)
(Continued)

(52) U.S. Cl.
CPC ......... *A01G 25/167* (2013.01); *G01N 27/223* (2013.01); *G01N 33/246* (2013.01); *G01R 27/26* (2013.01)

(58) Field of Classification Search
CPC ................ G01N 33/24; G01N 33/246; G01N 2033/245; G01N 22/04; G01N 27/048;
(Continued)

(56) References Cited

U.S. PATENT DOCUMENTS

| 4,219,776 A | * | 8/1980 | Arulanandan | ......... G01R 27/26 |
| | | | | 324/323 |
| 4,445,788 A | * | 5/1984 | Twersky | ................ G01K 1/026 |
| | | | | 374/142 |

(Continued)

FOREIGN PATENT DOCUMENTS

WO 2012052165 A1 4/2012

*Primary Examiner* — Thang X Le
(74) *Attorney, Agent, or Firm* — Greenberg Traurig, LLP

(57) ABSTRACT

A soil sensor assembly and methods of measuring undisturbed soil are disclosed. The soil sensor assembly can be a volumetric water content (VWC) sensor. The soil sensor assembly can include at least one soil probe. The soil probes can be secured to a support to enable an installation of the soil sensor assembly in a target soil. The soil probes can include helical blades secured concentrically along the support at predefined longitudinal locations. The soil probes can include at least one radiofrequency (RF) electrode secured to the helical blades at a predefined radial distance from a longitudinal axis of the support. The soil sensor assembly can also include at least one electronics unit coupled to the RF electrodes to receive and/or transmit RF signals from the RF electrodes. The soil sensor assembly can enable a self-tapping installation action and/or enable alienating the soil measurements (e.g., by RF electrodes) away from a disturbed soil.

13 Claims, 15 Drawing Sheets

Related U.S. Application Data

(60) Provisional application No. 62/339,970, filed on May 23, 2016, provisional application No. 62/262,670, filed on Dec. 3, 2015.

(51) Int. Cl.
*G01N 33/24* (2006.01)
*G01N 27/22* (2006.01)

(58) Field of Classification Search
CPC .. G01N 27/223; G01N 27/301; G01N 27/333; G01R 27/26; A01G 25/167
See application file for complete search history.

(56) References Cited

U.S. PATENT DOCUMENTS

| | | | | |
|---|---|---|---|---|
| 4,492,111 | A * | 1/1985 | Kirkland | G01N 3/48 324/323 |
| 4,929,885 | A * | 5/1990 | Dishman | G01N 27/223 324/664 |
| 5,442,293 | A * | 8/1995 | Lange | G01N 27/223 324/332 |
| 6,076,396 | A * | 6/2000 | Dadachanji | G01N 27/043 73/73 |
| 8,915,131 | B2 * | 12/2014 | Aughton | G01N 33/246 73/152.01 |
| 2002/0027438 | A1 * | 3/2002 | Ott | G01V 3/15 324/327 |
| 2004/0083833 | A1 | 5/2004 | Hitt et al. | |
| 2015/0168594 | A1 | 6/2015 | Chang | |

* cited by examiner

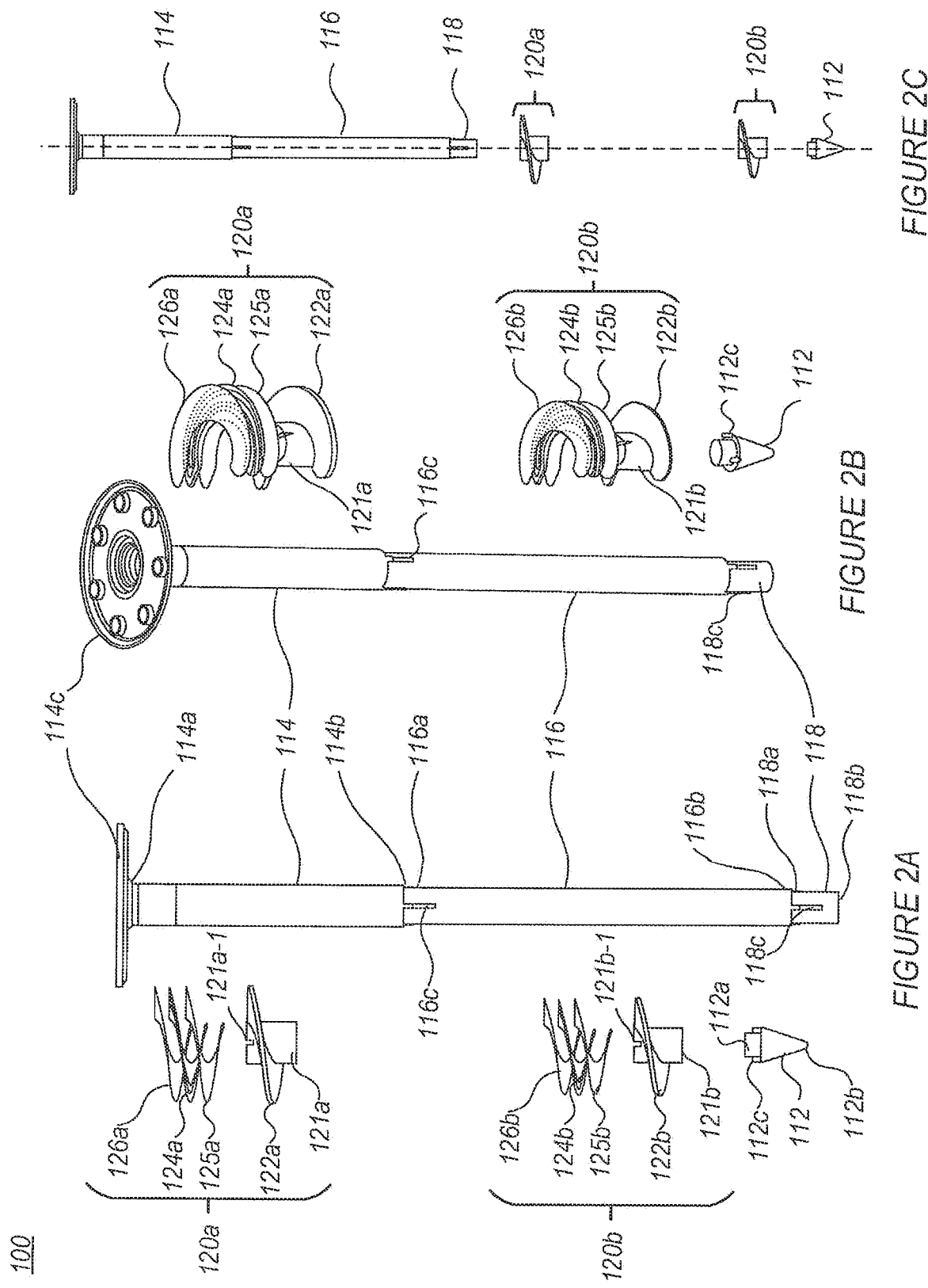

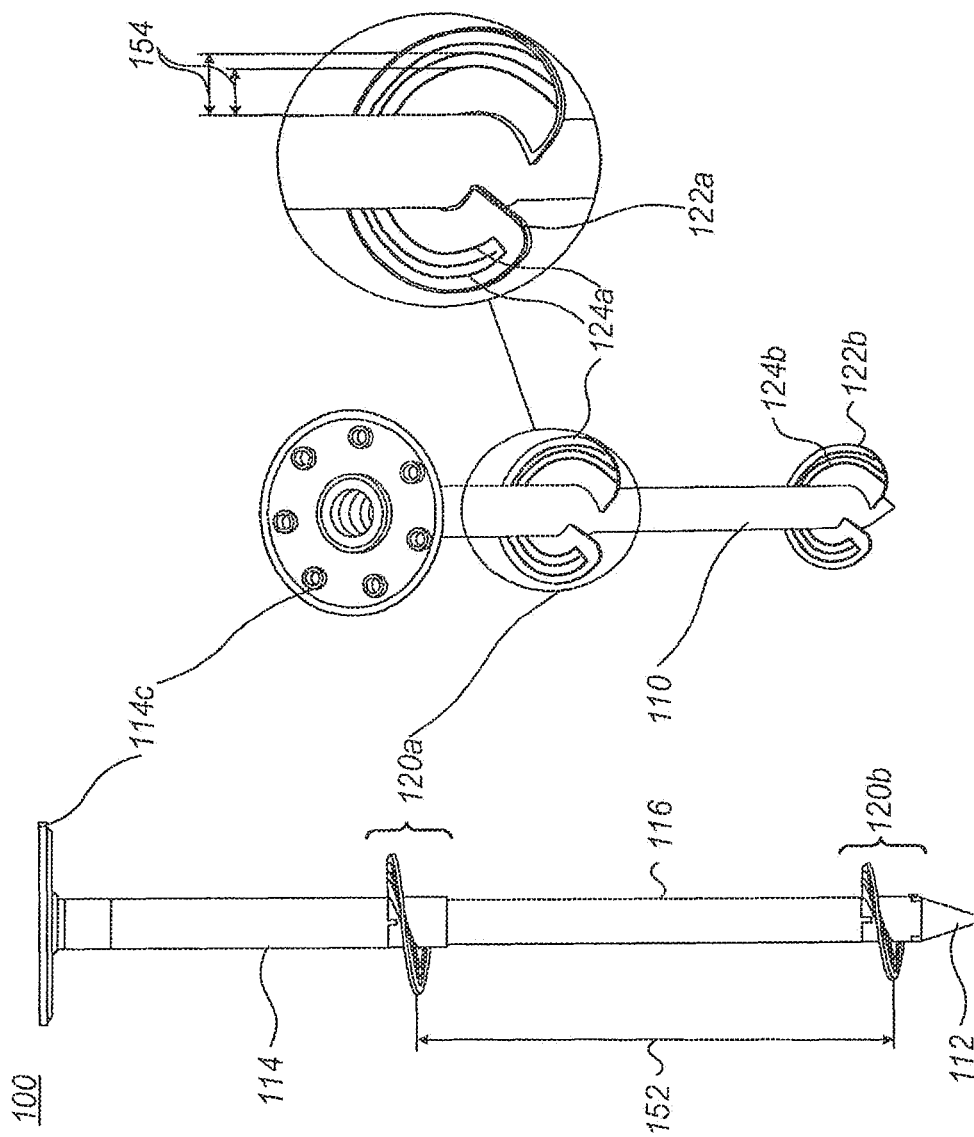

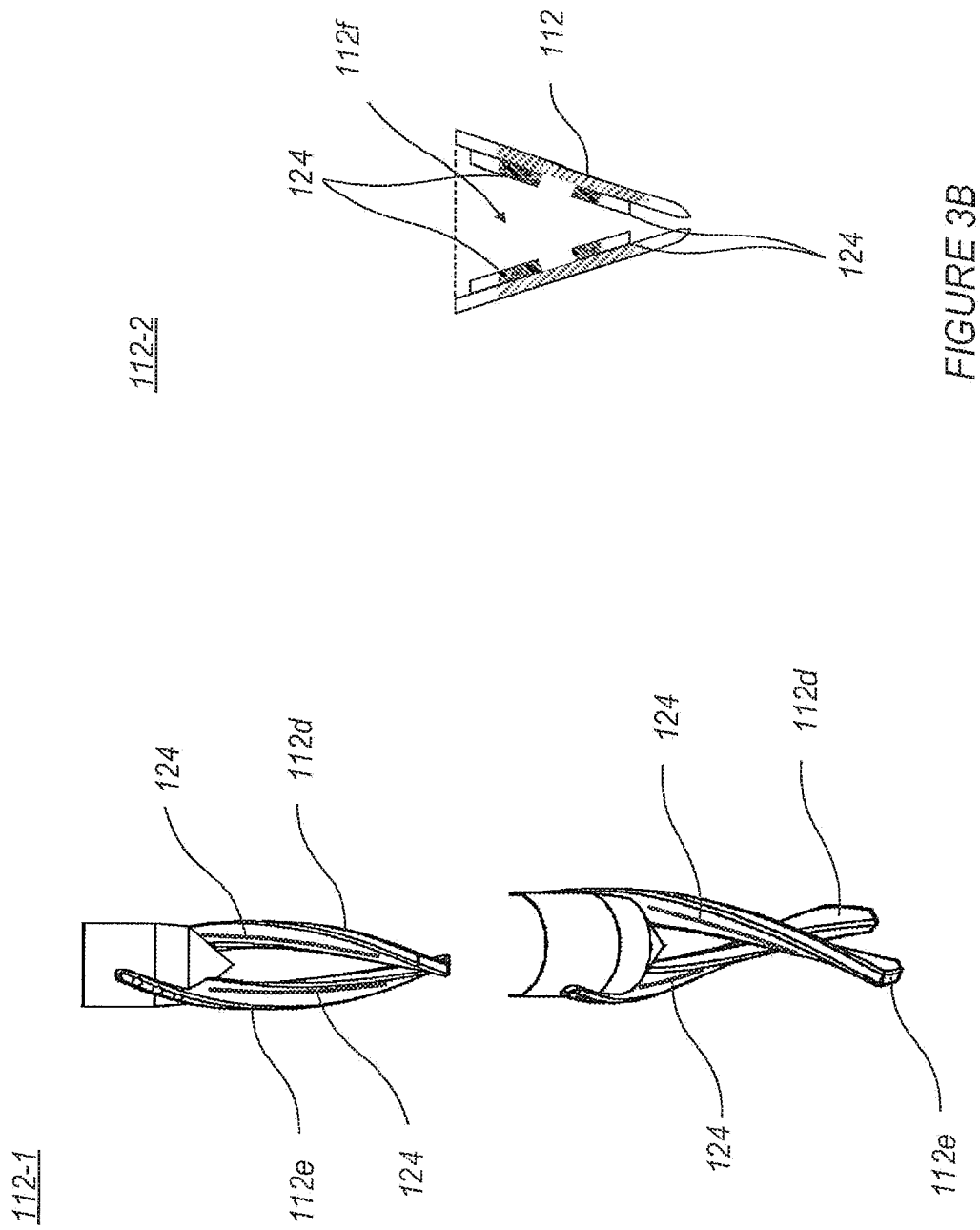

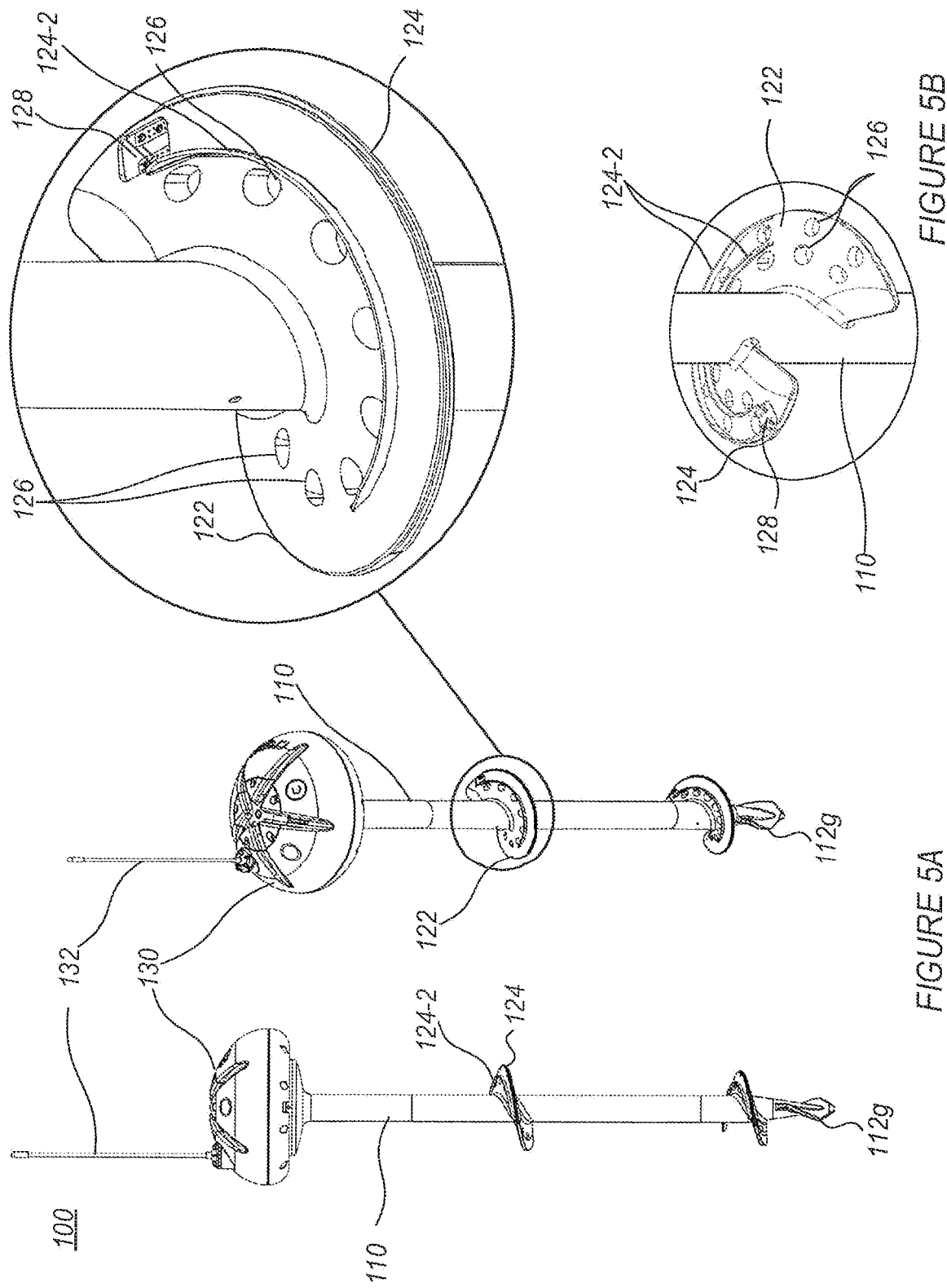

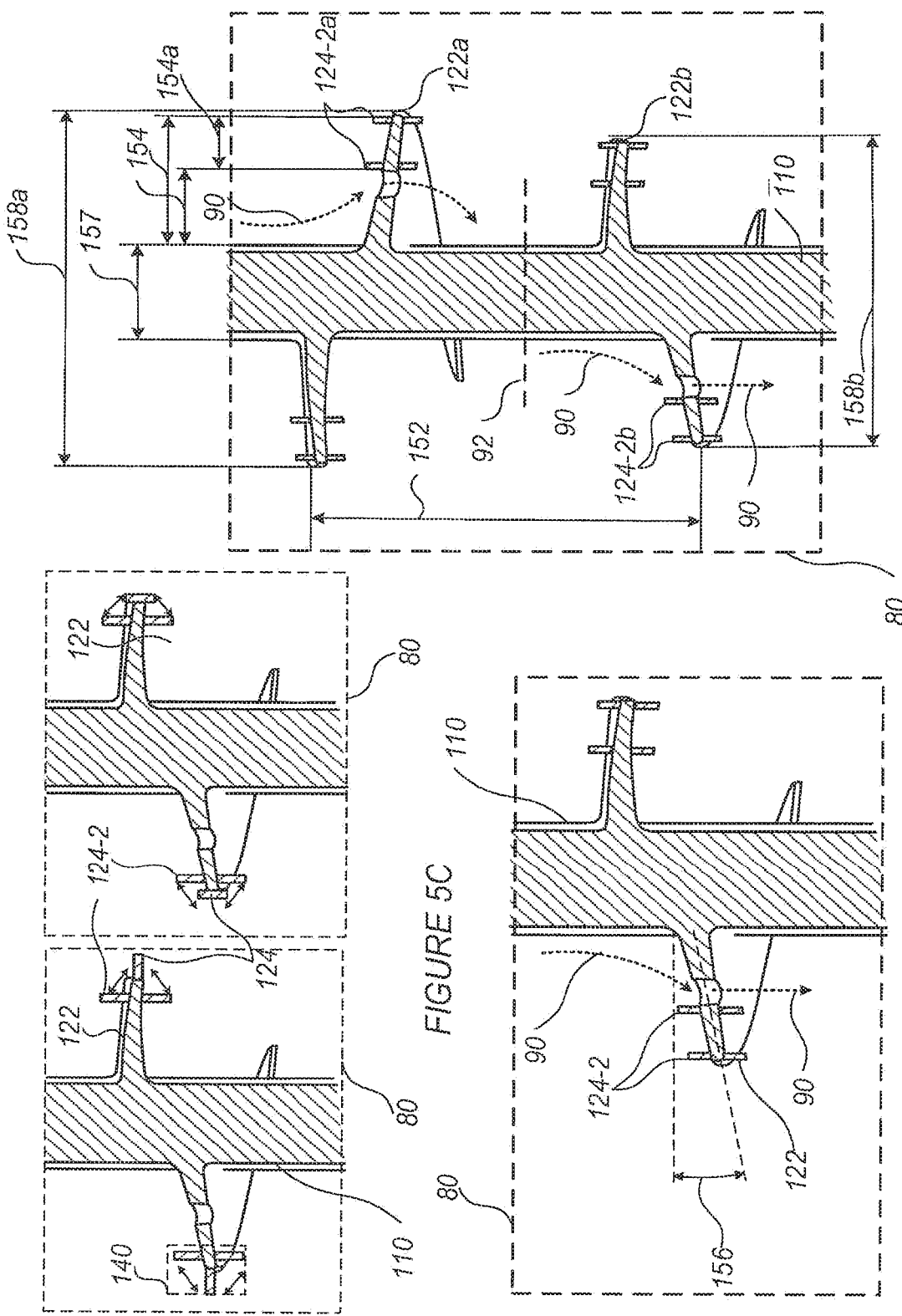

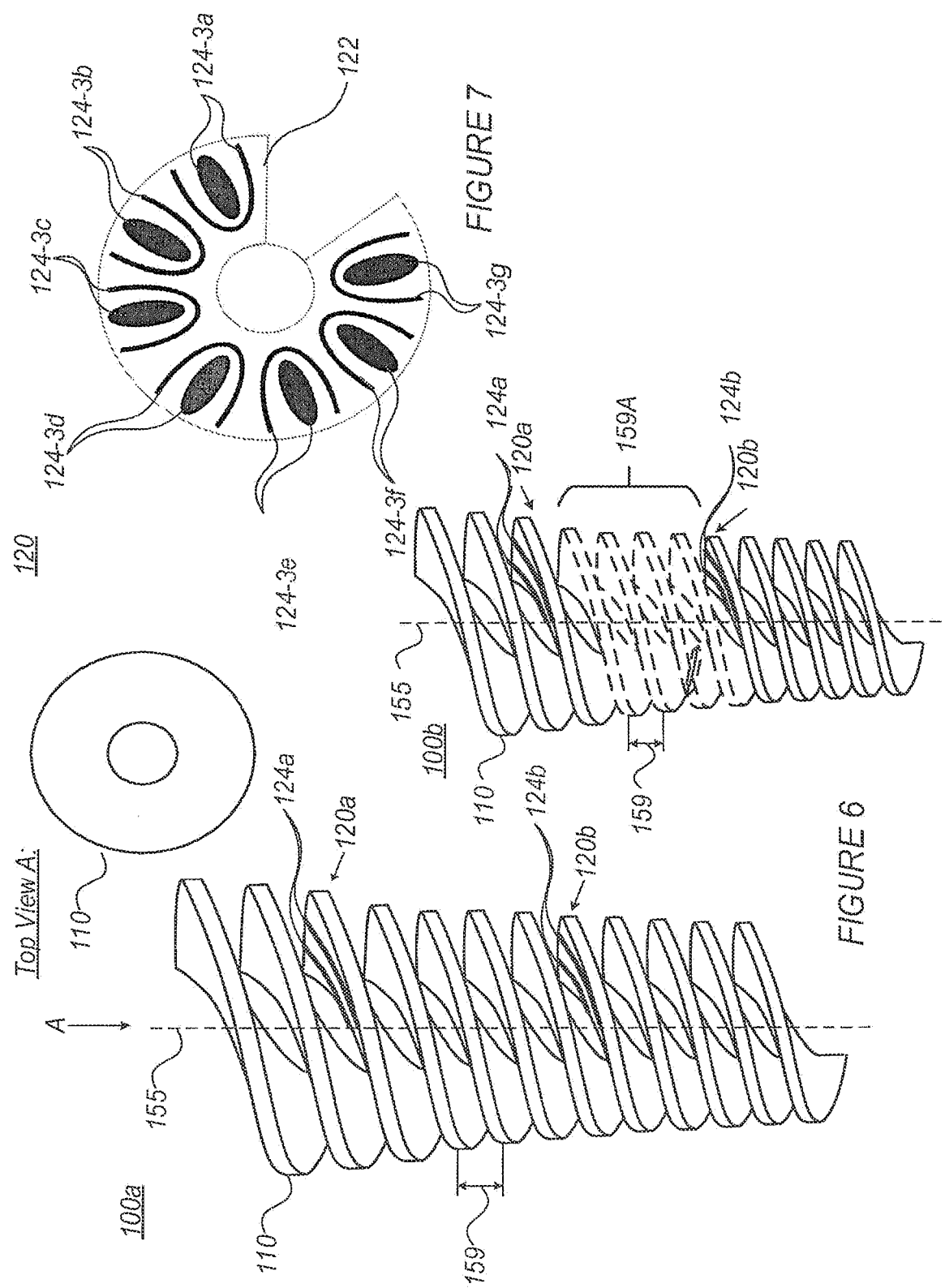

300

| PROVIDING A SOIL SENSOR ASSEMBLY INCLUDING: A ROTATABLY ANCHORABLE PORTION TO BE ROTATABLY ANCHORED IN A SOIL; AND AT LEAST ONE SOIL SENSOR MOUNTED ONTO THE ROTATABLY ANCHORABLE PORTION | ⌒ 310 |

↓

| ROTATABLY INSERTING THE SOIL SENSOR ASSEMBLY INTO A SOIL ALONG AN ANCHORING AXIS, THEREBY ANCHORING THE SOIL MOISTURE SENSING ASSEMBLY IN THE SOIL | ⌒ 320 |

FIGURE 11

SOIL SENSOR ASSEMBLY

BACKGROUND OF THE INVENTION

1. Technical Field

The present invention discloses a rotatably anchorable soil sensor, which provides an easy means of unbiased measuring of undisturbed soil.

2. Discussion of Related Art

Current volumetric water content (VWC) profile sensors can include a pole and/or circular radiofrequency (RE) electrodes wrapped around the pole. Typically, current VWC sensors can significantly disturb a target soil during an installation and/or can require pre-drilling procedures in order to be installed. Unmatched pre-drilling and VWC sensor's dimensions can result in a poor contact between the VWC sensor and the soil. The poor contact between the moisture sensor and the soil and/or disturbed soil can introduce measurement errors. For example, a gap can be generated between the VWC, sensor and the soil, in which vertical water flow and/or accommodation can occur, thereby affecting the VWC measurement of the target soil. Moreover, the pre-drilling requirement can increase the installation costs.

SUMMARY OF THE INVENTION

One aspect of the present invention provides a soil sensor assembly including: a rotatably anchorable portion to be rotatably anchored in a soil; at least one soil sensor mounted onto the rotatably anchorable portion; and a communicator for communicating at least one output of the at least one soil sensor to a location remote from the at least one soil sensor assembly.

Another aspect of the present invention provides a volumetric water content (VWC) sensor including: a support to enable installation of the VWC sensor in a target soil; at least one VWC probe positioned at a predefined longitudinal location along the support, the at least one VWC probe including: a helical blade secured along its inner lateral side to an outer surface of the support, and at least one radiofrequency (RE) electrode secured to the helical blade at a predefined radial distance from the support; and at least one electronics unit coupled to the at least one RF electrode to transmit and receive RF signals from the at least one RF electrode.

Another aspect of the present invention provides a volumetric water content (VWC) sensor comprising: at least one VWC probe including at least two radiofrequency (RF) electrodes, the at least one VWC probe to measure a VWC of a target soil in a measurement region between the at least two RF electrodes, and a support to secure positioning of the at one VWC probe, wherein the support occupies less than 10% of the measurement region.

These, additional, and/or other aspects and/or advantages of the present invention are set forth in the detailed description which follows; possibly inferable from the detailed description; and/or learnable by practice of the present invention.

BRIEF DESCRIPTION OF THE DRAWINGS

For a better understanding of embodiments of the invention and to show how the same may be carried into effect, reference will now be made, purely by way of example, to the accompanying drawings in which like numerals designate corresponding elements or sections throughout.

In the accompanying drawings:

FIGS. 2A-2E are illustrations of disassembled volumetric water content (VWC) sensor, according to some embodiments of the invention;

FIGS. 3A-3B are illustrations of various configurations of a tip of volumetric water content (VWC) sensor, according to some embodiment of the invention;

FIGS. 5A-5E are illustrations of a volumetric water content (VWC) sensor including radiofrequency (RF) electrodes protruding above at least one surface of helical blades, according to some embodiments of the invention.

FIG. 6 is an illustration of configuration of volumetric water content (VWC) sensor with a support being a coreless helical blade, according to some embodiments of the invention;

FIG. 7 is an illustration of a volumetric water content (VWC) probe including segmented RF electrodes, according to some embodiments of the invention;

FIG. 11 is a flowchart illustrating a method of installing a soil sensor assembly, according to some embodiments of the invention;

DETAILED DESCRIPTION OF THE INVENTION

Effective agriculture can depend on obtaining accurate, continuous, in-field soil measurements, for example soil moisture measurements, including soil measurements at different sub-surface depths. A target soil can be not uniform and therefore continuous measurements can be required to be measured at multiple locations in a field to best inform agricultural actions. For example, different parts of the field can require different amounts of irrigation, which can require continuous sod-moisture monitoring at different specific locations in the field. Current soil sensor devices can invariably provide biased measurements of sub-soil due to the disturbance of the soil, caused by, for example, their installation. Current scientific installation procedures that can provide, for example, unbiased measurements, can be complex and impractical in a working agricultural field. Current soil sensor devices do not provide practical, accurate, continuous and/or in-field soil measurements of subsurface soil. The present invention describes a soil sensor device, which can provide continuous, unbiased measurement of un-disturbed sub-surface soil, and/or can include a simple do-it-your self installation.

Figure 1A:
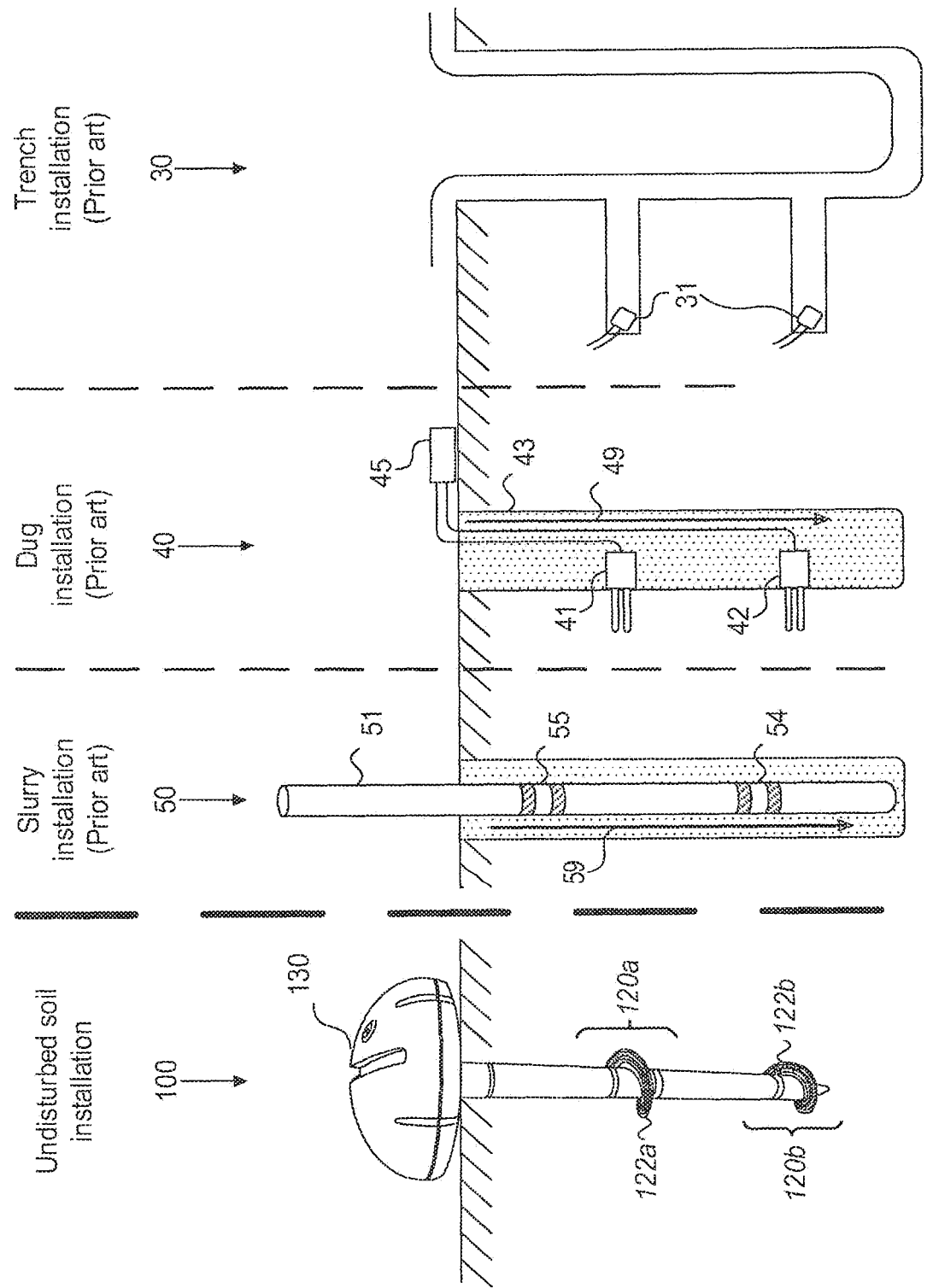
FIG. 1A is an illustration of a rotatably anchorable sensor and its undisturbed soil installation, according to some embodiments of the invention (on a left-hand side of FIG. 1A) and current soil sensors and installation methods of slurry installation of a profiling sensor, dug installation of scientific sensors and trench installation of scientific sensor, according to the prior art.

FIG. 1A presents a rotatably anchorable sensor 100 and its undisturbed soil installation 105, according to some embodiments of the invention (on a left-hand side of FIG. 1A) and current soil sensors and installation methods of slurry installation 50 of a profiling sensor, dug installation 40 of scientific sensors and trench installation 30 of scientific sensor, according to the prior art.

Slurry installation 50 can typically include drilling a wide-bore vertical hole, preparing slurry by mixing the soil from the hole with water, pouring the slurry back into the hole, and/or placing a pole-shaped profiling sensor 51 into the into slurry-filled vertical hole. The profiling sensor 51 can be therefore in contact with slurry 52, ensuring close contact of top sensor 53 and bottom sensor 54 with the slurried soil. One disadvantage of slurry installation can be that slurry 52 is a disturbed soil medium, which can enhance a vertical flow 59 of water through the slurry 52, thereby biasing the measurements of the sensors 55, 54. For example, measurements of bottom sensor 54 can be prone to reflect soil moisture that can be actually that of top soil due to, for example, excessive vertical flow 59 of water, through the slurry 52. Typically, following an irrigation event, measurements from the bottom sensor 54 can erroneously show a rise in soil moisture that can be similar in timing and amplitude, to measurements of the top sensor 55. Such measurements can be biased, since water takes time to filtrate down through undisturbed soil, as is well known in the art.

Dug installation can include a vertical hole being dug, through which the sensors, e.g., top scientific sensor 41 and bottom scientific sensor 42, can be placed at different desired depths, such that their sensing part, e.g., prongs, are pierced into the wall of the hole to measure intact soil. The sensors 41 and 42 can be typically connected by wire to a logger 45 on the ground, and the hole is then filled with soil-fill 43. One disadvantage of dug installation method can include disturbed soil-fill 43, through which a vertical flow 49 of water can occur. Thereby, bottom scientific sensor 42 can give erroneous measurements that correspond in timing and amplitude to those of top scientific sensor 41, reflecting unnaturally excessive vertical flow 49 of water through the soil fill 43. Another disadvantage of dug installation 40 can include difficult and time-consuming installation.

Trench installation 30 can provide a scientifically robust method for installing scientific sensors 31. One disadvantage of the trench installation can include impractical implementation in an active agricultural field. In this method, a deep trench, Trench installation can typically include drilling one yard deep and wide, dug and/or wide bore (e.g., 60 cm) vertical peers into a wall of the trench at the desired depths, and/or manually placing scientific sensors through the vertical peers, and/or piercing their sensing prongs into undisturbed soil at the far end of the peer, at an upward angle of 45 degrees, so that no seepage of water through the peer to affect the sensor prongs can occur. The trench can be covered with a tarp, to prevent accumulating water to enter the peers, and/or accumulated water to be pumped from the tarp covered trench. Trench installation 30 can avoid bias of disturbed soil and vertical flow, however it can be utterly impractical in the setting of an agricultural field, more so when multiple measurements are needed from different parts of a field.

Currently available soil sensor devices can provide biased measurements, due to measuring disturbed soil, and/or due to biased vertical water flow. While the description above is of soil moisture measurements, the same can be true for other measurements that can include soil nutrients, micro nutrients, genetic measurements, organic compounds, and many other measurements.

The present invention discloses a rotatably anchorable spiral sensor 100, which can be installed into sub-surface soil 105, and/or provide unbiased, measurements from undisturbed soil. The disclosed spiral sensor 100 can include sensors 120 at multiple depths, such as a top sensor 120a located on, or integrated into a helical blade 122a, and/or a sensor 120b located on or integrated helical blade 122b. Spiral sensor 100 can be installed by rotating it into the subsurface soil 105, and so both helical blades 122a, 122b can be cut into the subsurface soil, thereby placing sensors 120a, 120b in direct contact with undisturbed soil, and providing unbiased measurements from the soil, measurements that are not subject to excessive vertical water flow. Installation of spiral sensor 100 does not require slurry and/or soil-fill, thereby no biased measurements due to vertical flow can occur. Sensors 120a, 120b can include helical blades 122a, 122b away from shaft 110 of the spiral sensor 100, thereby minimizing possible vertical flow along shaft 110 to bias the readings of the sensor. In some embodiments, a shape of electronics bay 130 of the spiral sensor and/or the shape of helical blades 122a, 122b can minimize vertical flow.

Spiral sensor 100 can provide accurate soil measurements of undisturbed soil and/or provide measurement that are not unbiased by artifactual vertical flow.

Advantageously, disclosed spiral sensor(s) 100 provide high quality results without disturbing the soil. In some embodiments, spiral sensor(s) 100 may be installed in a simple manner and using five to ten fold shorter installation time with respect to the prior art, for example in the order of magnitude of minutes or tens of minutes instead of hours. Advantageously, in some embodiments, disclosed spiral sensor(s) 100 may revolutionize the domain of soil sensors, offering for the first time, a device that provides continuous, accurate, soil measurements of undisturbed soil, unbiased by inadvertent vertical water flow, and with an unprecedented simplicity and speed of a truly do-it-yourself installation.

A soil sensor assembly and methods of measuring undisturbed soil are disclosed. The soil sensor assembly can be a volumetric water content (VWC) sensor. The soil sensor assembly can include at least one soil probe. The soil probes can be secured to a support to enable an installation of the soil sensor assembly in a target soil. The soil probes can include helical blades secured concentrically along the support at predefined longitudinal locations. The soil probes can include at least one radiofrequency (RF) electrode secured to the helical blades at a predefined radial distance from a longitudinal axis of the support. The soil sensor assembly can also include at least one electronics unit coupled to the RE electrodes to receive and/or transmit RE signals from the RE electrodes. The soil sensor assembly can enable a self-tapping installation action and/or enable alienating the soil measurements (e.g., by RF electrodes) away from a disturbed soil. The soil sensor assembly can enable measuring properties of undisturbed soil and/or eliminate a vertical water flow along the sensor thereof.

Figure 1C:
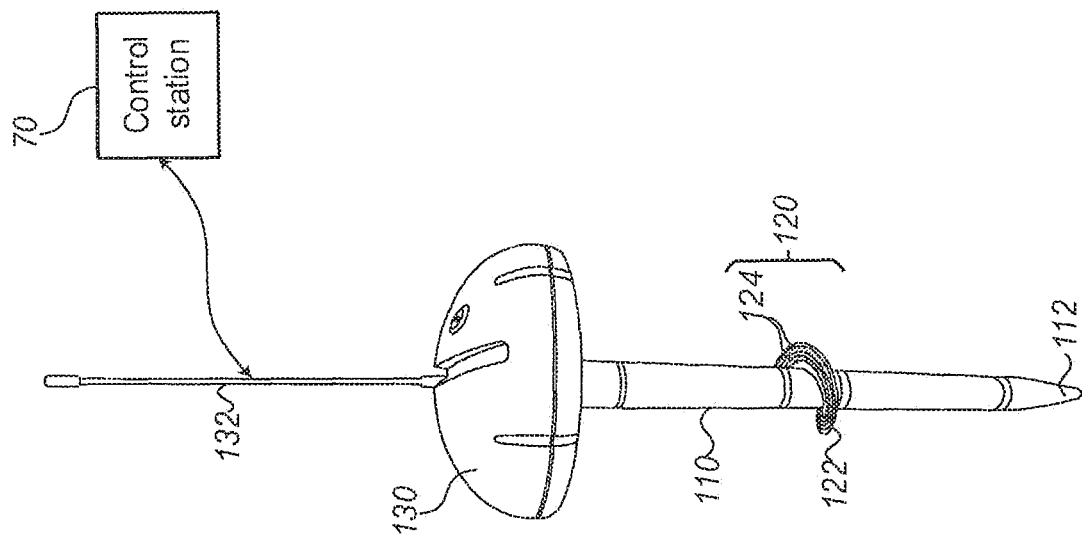
FIGS. 1B-1C are illustrations of a volumetric water content (VWC) sensor, according to some embodiments of the invention.
Figure 1B:
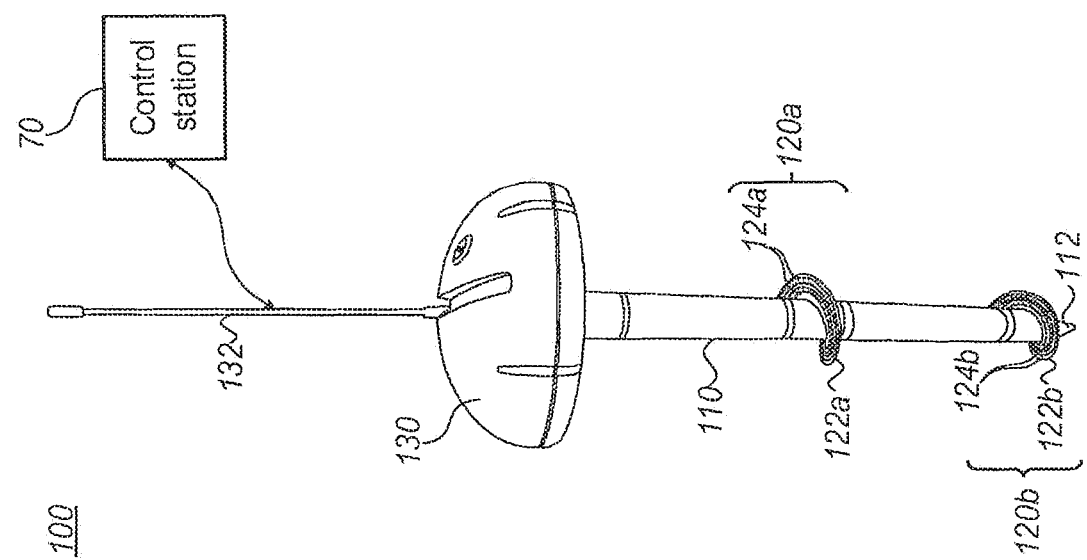

FIGS. 1B-1C are illustrations of a volumetric water content (VWC) sensor 100, according to some embodiments of the invention. VWC sensor 100 can include a support 110. In some embodiments, support 110 is a rotatably anchorabable portion. In some embodiments, support 110 can be a pole (e.g., as illustrated in FIGS. 1B-1C). In some embodiments, pole 110 is a monolith having a tapered nail-like shape and/or includes a tip 112. Tip 112 can have a tapered shape that can enable initial penetration of VWC sensor 100 into a target soil during an installation process.

VWC sensor 100 can include at least one VWC probe 120 secured to an outer surface of pole 110 at predefined longitudinal location along the pole. In some embodiments, VWC sensor 100 includes single VWC probe 120, as shown in FIG. 18. In some embodiments, VWC sensor 100 includes two VWC probes 120a, 120b separated by a longitudinal distance 152 (e.g., as shown in FIG. 1B, FIG. 2D) that enable measuring VWC of a target soil at two depths (e.g., profile VWC sensor) in some embodiments, VWC sensor 100 also includes at least one additional soil sensor, for example, a temperature sensor, a pH sensor, a pressure sensor, a salinity sensor and/or sensor for determining level of minerals in a target soil.

In some embodiments, each of VWC probes 120 (e.g., each of VWC probes 120a, 120b as shown in FIG. 1B) includes a helical blade 122 secured along an inner lateral side to an outer surface of pole 110. Helical blade 122 can complete a helical path of at least 360° around pole 110. In some embodiments, helical blade 122 can complete 720° around pole 110. A shape of helical blade 122 can enable performing a screwing motion of VWC sensor 100 within a target soil during an installation process.

VWC probe 120 (e.g., each of VWC probes 120a, 120b as shown in FIG. 1B) can include radiofrequency (RF) electrodes 124 secured to helical blade 122 at a predefined radial distance 154 from pole 110 (e.g., as shown in FIG. 2E). RF electrodes 124 can have a helical shape that corresponds to shape of helical blade 122 and/or can complete a helical path of at least 360° around pole 110. RF electrodes 124 can be surface electrodes and/or can be secured to at least one of surfaces of helical blade 122. In some embodiments, RF electrodes 124 can be embedded within helical blade 122. RF electrodes 124 can cover at least a portion of the surfaces thereof. An RF field can be generated by adjacent RF electrodes 124 to measure a VWC of a target soil in a measurement region between the adjacent RF electrodes. In some embodiments, helical blade 122 is a RF electrode.

Radial distance 154 can be predefined based on a desired RF field to be generated by RF electrodes 124 and/or to alienate RF electrodes 124 from pole 110 and/or from a disturbed target soil. In some embodiments, RF electrodes 124 are positioned at 30% most lateral portion of helical blades 122.

During a screwing motion of an installation process, helical blade 122b of VWC probe 120b enters an undisturbed target soil, thereby providing a good contact between helical blade 121b and/or RF electrodes 124b and the target soil. Longitudinal distance 152 between helical blades 122a, 122b and/or diameters of helical blades 122a, 122b can be predefined to, for example, optimize the accuracy of VWC measurement of the target soil and/or to provide a good contact between helical blade 122a and/or RF electrodes 124a and the target soil. For example, a diameter of helical blade 122a can be greater than a diameter of helical blade 122b (e.g., as shown in FIG. 1B) such that helical blade 122a, which can follow a screwing path of helical blade 122b during the screwing motion of the installation process, enters a undisturbed soil, thereby providing a good contact between helical blade 122a and/or RF electrodes 124a and a target soil.

Figure 8:
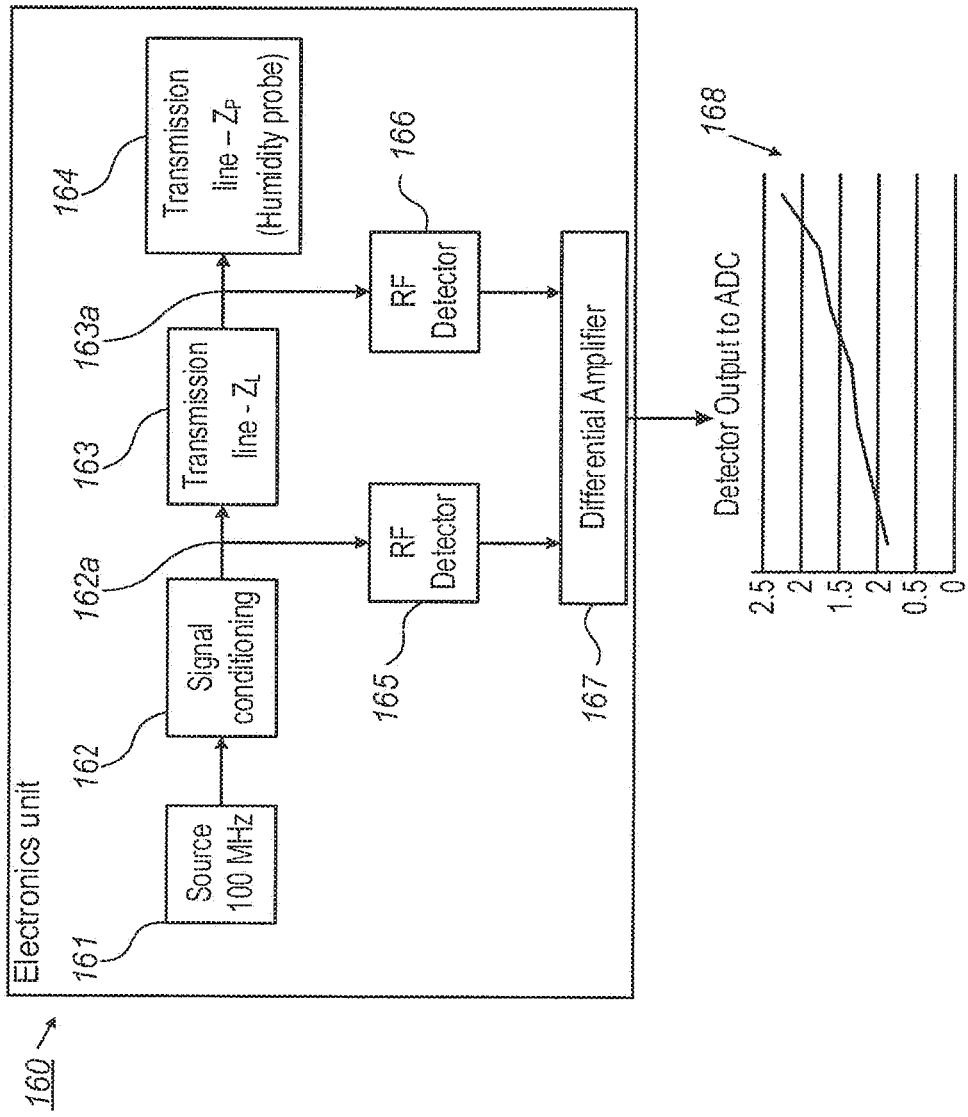
FIG. 8 is a schematic block diagram illustrating an electronics unit of volumetric water content (VWC) sensor, according to some embodiments of the invention.
Figure 9:
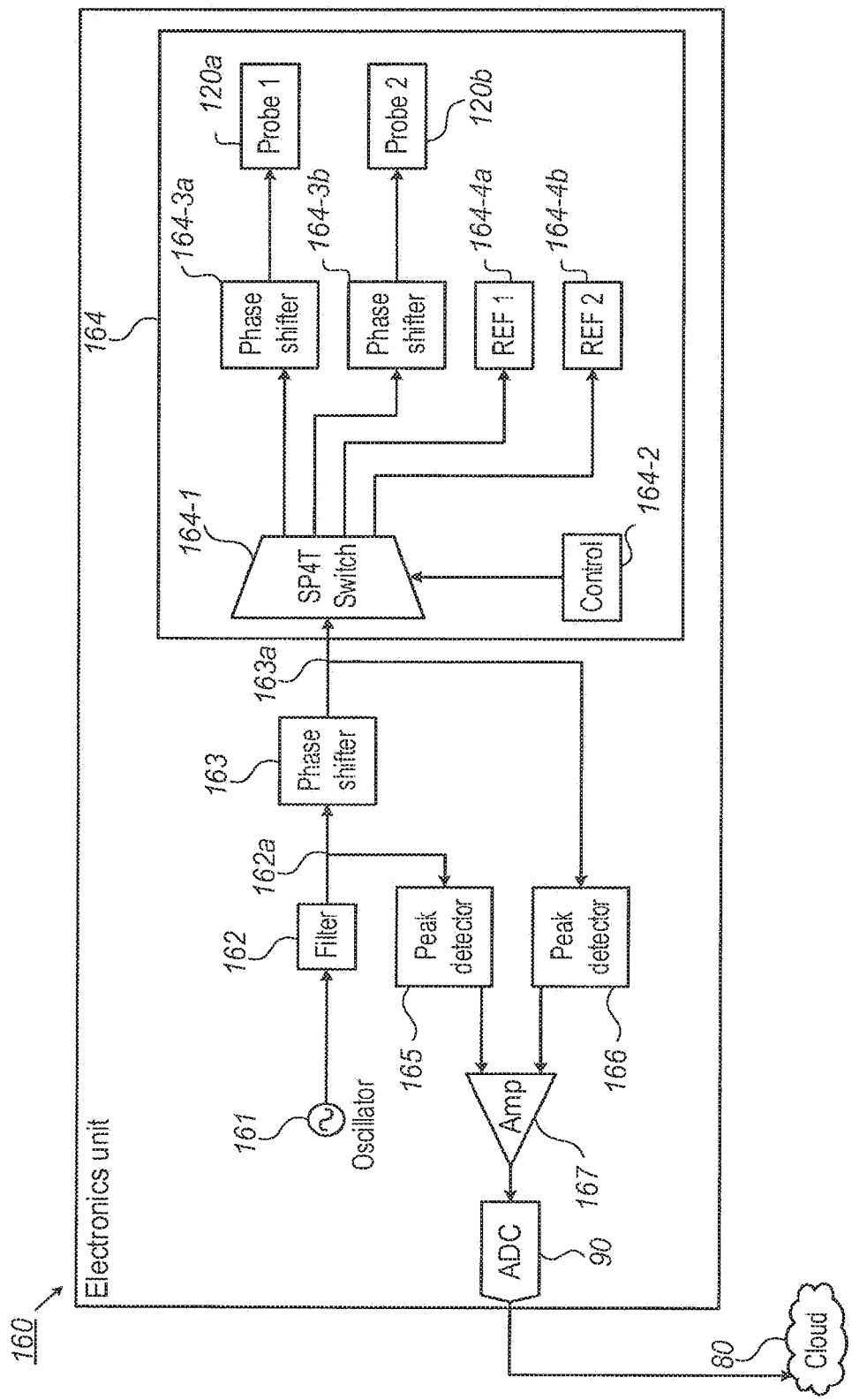
FIG. 9 is a schematic block diagram of an electronic circuitry of electronics unit of volumetric water content (VCW) sensor, according to some embodiments of the invention.

VWC sensor 100 can include at least one electronics unit (e.g., electronics unit 160 as shown in FIGS. 8-9) that can transmit and/or receive RF signals from RF electrodes 124. In some embodiments, at least one of the electronics units is embedded within pole 110. In some embodiments, at least one of the electronics units is embedded within helical blade 122 of at least one of VWC probes 120. In some embodiments, VWC sensor 100 includes an electronics bay 130 secured to pole 110 at the end being opposite to tip 112. Electronics bay 130 can include at least one of the electronics units. RF electrodes 124 of VWC probe 120 can be connected to the electronic units and/or to electronics bay 130 using wiring and/or wireless connections (not shown). In some embodiments, electronics bay 130 includes an antenna 132. In some embodiments, electronics units and/or electronics bay 130 include a wireless communications device (e.g., wireless communicator) that can enable transmitting the received RF signals (e.g., by antenna 1321 to a remote control station 70. The wireless communications device can be any wireless communications device as is known in the art.

FIGS. 2A-2C are illustrations of disassembled volumetric water content (VWC) sensor 100 according to some embodiments of the invention. FIGS. 2D-2E are illustrations of assembled VWC sensor 100, according to some embodiments of the invention. FIGS. 2A, 2C, 211 provide a side view and FIGS. 2B, 2E provide an isometric view of VWC sensor 100.

In some embodiments, pole 110 of VWC sensor 100 includes a first tubular section 114, a second tubular section 116 and/or a third tubular section 118. First tubular section 114 can have a first end 114a and a second end 114b, second tubular section 116 can have a first end 116a and a second end 116b and/or third tubular section 118 can have a first end 118a and a second end 118b.

In some embodiments, first end 114a of first tubular section 114 includes connector 114c that can connect electronics bay 130 to pole 110. Connector 114c can include any connection means known in the art. In some embodiments, second tubular section 116 proceeds coaxially from second end 114b of first tubular section 114 and/or third tubular 118 section tubular section proceeds coaxially from second end 116b of second section 116. Diameters and lengths of first tubular section 114, second tubular section 116 and/or third tubular section 118 can be predefined to provide a tapered shape for pole 110. For example, as shown in FIGS. 2A-2E, diameter of second tubular section 116 can be smaller than diameter of first tubular section 114 and/or diameter of third tubular section 118 can be smaller than diameter of second tubular section 116. In some embodiments, first tubular section 114 has diameter of 30 mm and/or length of 177 mm, second tubular section 116 has diameter of 26 mm and/or length of 250 mm and/or third tubular section 118 has diameter of 20 mm. In some embodiments, pole 110 and/or each of tubular sections 114, 116 and/or 118 include a screw-thread to enhance a screw motion of VWC sensor 100 during the installation process.

In some embodiments, first end 116a of second tubular section 116 includes connectors 116c and/or first end 118a of third tubular section 118 includes connectors 118c. Connectors 116c, 118c can be protrusions and/or can be located equally about an outer surface of pole 110 (e.g., as shown in FIGS. 2A-2C).

In some embodiments, VWC sensor 100 includes a first VWC probe 120a and a second VWC probe 120b. Helical blade 122a of first VWC probe 120a can be connected to an outer surface of a cylindrical shell 121a and/or helical blade 122b of second VWC probe 120b can be connected to an outer surface of a cylindrical shell 121b. Cylindrical shells 121a, 121b can have diameters that match the diameters of second and third tubular sections 116, 118, respectively. Cylindrical shells 121a, 121b can also include matching connectors 121a-1, 121b-1 (e.g., indents as illustrated in FIGS. 2A-2C) that can be connected to connectors 116c, 118c and can secure first and second VWC probes 120a, 120b to pole 110.

In some embodiments, tip 112 of VWC sensor 100 has a first end 112a and a second end 112b. First end 112a can have a diameter that match the diameter of second end 118b of third tubular section 118. First end 112a of tip 112 can also include connectors 112c (e.g., protrusions as shown in FIGS. 2A-2C) and/or shell 121b of second VWC probe 120b can include matching connectors 118d (e.g., indents as shown in FIGS. 2A-2C) such that tip 112 can be connected and/or secured to third tubular section 118 and/or to shell 121b of second VWC probe 120b. In some embodiments, second end 112b of tip 112 has a tapered shape that can al low for, for example, VWC sensor 100 to penetrate to a target soil during an installation procedure.

In some embodiments, connectors 112c, 116c, 118c and/or 118d include catches know in the art (e.g., detents) that can enhance securing of VWC probes 120 and tip 112 to pole 110.

The diameter of first VWC probe 120a that can match the diameter of second tubular section 116, the diameter of second VWC probe 120a that can match the diameter of third tubular section 118 and/or the diameter of first end 112a of tip 112 that can match the diameter of second end 118b of third tubular section 118 can simplify the assembly of VWC sensor 100, as shown in FIG. 2C The assembled VWC sensor 100 is shown in FIGS. 2D-2E.

In some embodiments, VWC probe 120 includes three layers: a first layer that includes helical blade 122, a second layer that includes RE electrodes 124 secured to a substrate 125, and a third protective layer 126 (e.g., as shown in FIGS. 2A-2B). Substrate 125 can be secured to helical blade 122. Protective layer 126 can cover BY electrodes 124 to provide a protection during an installation of VWC sensor 100 within a target soil. In some embodiments, RF electrodes 124 are secured to helical blade 122 (without substrate 125). In some embodiments, helical blade 122 of VWC probe 120 completes a helical path of at least 360° around pole 110. In some embodiments, RF electrodes 124 have a helical shape that corresponds to shape of helical blade 122 and/or complete a helical path of at least 360° around pole 110.

FIGS. 3A-3B are illustrations of various configurations of a tip 112 of a volumetric water content (VWC) sensor 100, according to some embodiments of the invention. FIG. 3A presents an isometric view and a side view of a tip 112-1. FIG. 3B present a cross-section view of tip 112-2.

In some embodiments, tip 112 includes at least two prongs 112d, 112e, where each prong 112d, 112e includes RF electrodes 124 as shown in FIG. 3A). Each prong 112d, 112e can have a helical shape and/or can include a nonconductive material. An RF field can be generated by RF electrodes 124 of each prong 122d, 122e to measure a VWC of a target soil in a measurement region between the RF electrodes.

In some embodiments, tip 112 has a gap 112f (e.g., as shown in FIG. 3B). Tip 112 can have a tapered end (e.g., tip 112-2 as shown in FIG. 3A). Tip 112-2 can include RE electrodes 124 secured to an inner lateral surface of the tip within gap 112f.

FIGS. 4A-4D are illustrations of various configurations of radiofrequency (RF) electrodes 124 of a volumetric water content (VWC) sensor 100, according to some embodiments of the invention. In some embodiments, two VWC probes 120a, 120b are positioned adjacently at a first predefined longitudinal location along pole 110 and/or two VWC probes 120c, 120d are positioned adjacently at a second predefined longitudinal location along pole 110 (see e.g., FIG. 4A). RF electrodes 124a, 124b of adjacent VWC probes 120a, 120b and/or RF electrodes 124c, 124d of adjacent VWC probes 120c, 120d can face each other. A RF field can be generated by facing RE electrodes 124a, 124b and/or facing RF electrodes 124c, 124d to measure a VWC of a target soil in measurement regions between the RF electrodes. A longitudinal distance between adjacent VWC probes 120a, 120b, a longitudinal distance between adjacent VWC probes 120c, 120d, the first longitudinal location and/or the second longitudinal location can be predefined to, for example, optimize the accuracy of moisture measurements of a target soil and/or to improve a contact between helical blades 122a, 122b, 122cb 122d and the target soil during a screwing motion of an installation process, as described above.

Figure 4B:
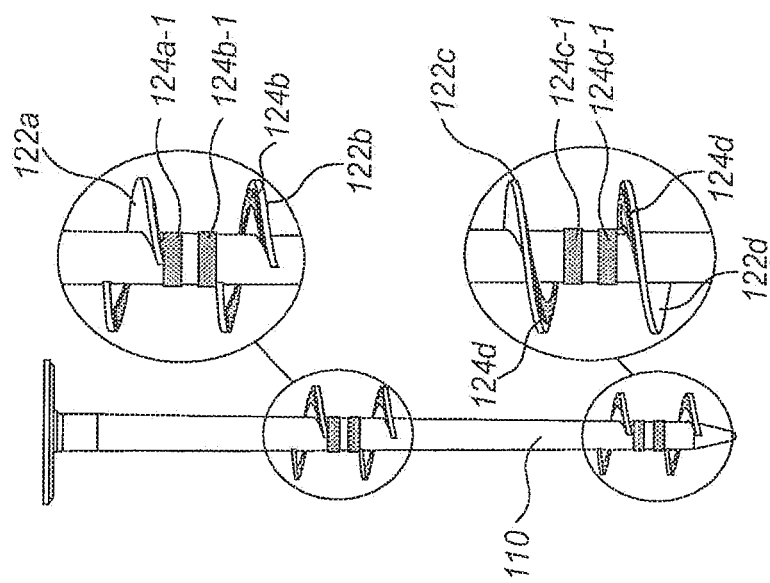
FIGS. 4A-4D are illustrations of various configurations of radiofrequency (RF) electrodes of a volumetric water content (VWC) sensor, according to some embodiments of the invention.
Figure 4A:
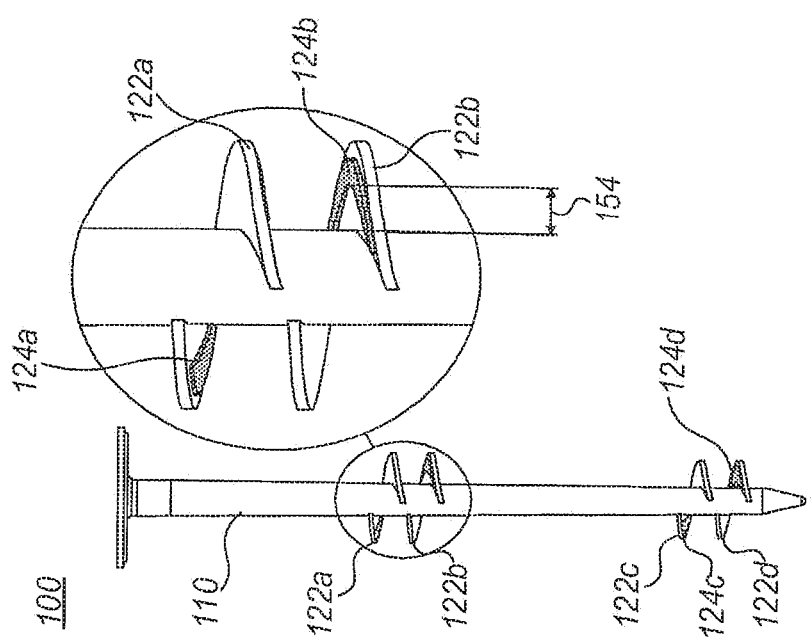
Figure 4D:
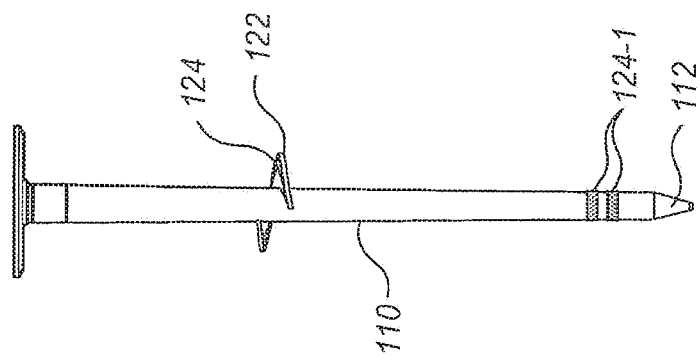
Figure 4C:
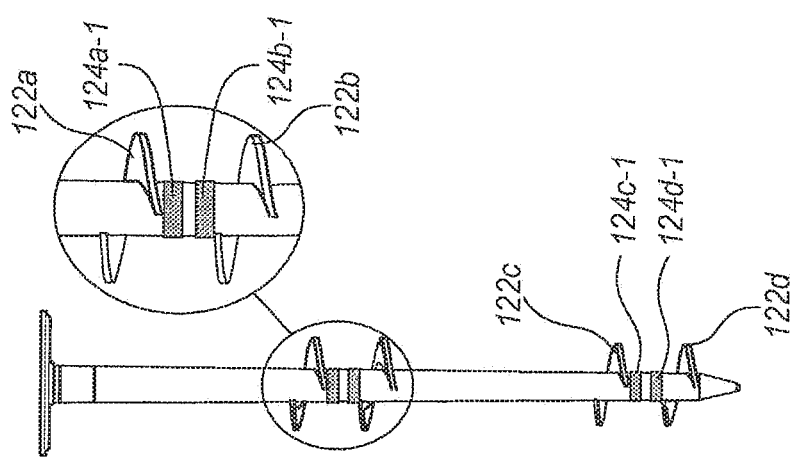

In some embodiments, VWC sensor 100 includes RF electrodes 124-1. RF electrodes 124-1 can be circular and/or can be secured to an outer surface of pole 110. RF electrodes 124-1 can be surface electrodes. In some embodiments, RE electrodes 124a-1, 124b-1 are positioned between two adjacent VWC probes 120a, 120b and/or RF electrodes 124c-1, 124d-1 are positioned between two adjacent VWC probes 120c, 120d at predefined longitudinal locations (e.g., as shown in FIG. 4B). In some embodiments, RF electrodes 124a-1, 124b-1 and/or RF electrodes 124c-1, 124d-1 are electrical continuations of respective VWC probes 120a, 120b and/or 120e, 120d. In some embodiments, RE electrodes 124-1 only are secured to pole 110 (without RF electrodes 124 secured to helical blades 122). For example, RF electrodes 124-1a, 124-1b, 124-1c, 124-1d as shown in FIG. 4C. In some embodiments, VWC sensor 100 includes at least one VWC probe 120 and/or RF electrodes 124-1, where VWC probe 120 can also include RF electrodes 124, as shown in FIG. 4D.

FIGS. 5A-5E are illustrations of a volumetric water content (VWC) sensor 100 including radiofrequency (RF) electrodes 124-2 protruding above at least one surface of helical blades 122, according to some embodiments of the invention. FIG. 5A present a side view and an isometric view of VWC sensor 100 (a left hand-side and a right-hand side, respectively). FIG. 5B presents an isometric blow-up view of VWC probe 120 of VWC sensor 100. FIGS. 5C-5E present a cross-section view of a portion of VWC sensor 100.

In some embodiments, tip 112 of VWC sensor 100 includes a helical blade 112g (e.g., as shown in FIG. 5A). In some embodiments, RF electrode 124 is secured to an outer lateral side of helical blade 122 of at least one VWC probe 120 (e.g., as shown in FIG. 5A). In some embodiments, at least one RF electrode 124-2 is embedded within helical blade 122 at a predefined radial distance from pole 110 such that embedded RF electrodes 124-2 protrude above at least one of surfaces of helical blade 122 (e.g., as shown in FIGS. 5A-5B). RF electrodes 124-2 can be three-dimensional electrodes and/or can have a helical shape that corresponds to shape of helical blade 122. An RF field can be generated by RF electrodes 124-2 and/or RF electrodes 124 to measure a VWC of a target soil 80 in a measurement region 140 between the RE electrodes, as schematically illustrated by arrows in FIG. 5C. In some embodiments, helical blade 122 and/or pole 110 occupies less than 10% of measurement region 140.

In some embodiments, a temperature sensor 128 is embedded within helical blade 122 of VWC probe 120, as shown in FIGS. 5A-5B. Temperature sensor 128 can include a thermal resistor and/or can measure a temperature of a target soil. The thermal resistor of temperature sensor 128 can be a part of electrical circuitry of electronics unit (e.g., electronics unit 160 shown in FIGS. 8-9) and/or can transmit information regarding the temperature by, for example, changing a DC level of RF signals generated by RF electrodes 124 and/or RF electrodes 124-2. In some embodiments, a plurality of sensors are embedded and/or secured to helical blades 122 of VWC probes 120, for example, a pH sensor, a pressure sensor, a salinity sensor and/or a sensor that can measure level of mineral in a target soil.

In some embodiments, helical blades 122 include a plurality of holes 126 positioned between pole 110 and protruding RE electrodes 124-2 and/or RF electrodes 124 (e.g., as shown in FIGS. 5A-5B). Holes 126 can drain a water 90 flowing along pole 110 and/or along helical blades 122 (e.g., as indicated by dashed arrows in FIG. 5D) to prevent accommodation of the water in a vicinity of RE electrodes 124-2 and/or RF electrodes 124 (e.g., as shown in FIG. 5D). In some embodiments, helical blades 122 are secured to pole 110 at an angle 156 with respect to the pole to provide a slope that facilitates drainage of flowing water 90 (e.g., as shown in FIG. 5D).

In some embodiments, pole 110 of VWC sensor 100 has a diameter 157 ranging between 10-40 mm (e.g., as shown in FIG. 5E) Helical blades 122 can have a diameter of 158 ranging between 80-120 mm. For example, diameter 158a of helical blade 122a can be greater than diameter 158b of helical blade 122b (e.g., as shown in FIG. 5E) such that helical blade 122a, which can follow a screwing path of helical blade 122b during a screwing motion of an installation process, enters a undisturbed soil, thereby providing a good contact between helical blade 122a and/or RF electrodes 124-2a and target soil 80.

In some embodiments, RF electrodes 124-2 (e.g., as shown in FIG. 5A) and/or RF electrodes 124 (e.g., as shown in FIGS. 1B-1C, FIGS. 2A-2E, FIGS. 4A-4D) positioned at predefined radial distance 154 from pole 110, as described above and schematically shown in FIG. 5E. Radial distance 154 can range between 18-40 mm and/or such that RE electrodes 124-2 and/or RE electrodes 124 being positioned at 30% most lateral portion of helical blades 122 (e.g., RF electrodes 124-2a, 124-2b secured to helical blades 122a 122b as shown in FIG. 5E). Radial distance 154 (e.g., radial distance of RF electrodes 124, 124-2 from pole 110) and/or a radial distance 154a between the RF electrodes (e.g., RF electrodes 124-2a embedded within helical blade 122a, as shown in FIG. 5E) can be defined based on a desired RF field to be generated to measure a VWC of a target soil 80.

In some embodiments, helical blades 122a, 122b of VWC probes 120a, 120b are secured to pole 110 and separated by longitudinal distance 152 (e.g., as shown in FIG. 5E). Longitudinal distance 152 can be predefined to, for example, optimize the accuracy of VWC measurement of a target soil 80 and/or to provide a good contact between helical blades 122a, 122b and the target soil during a screwing motion of an installation process. For example, longitudinal distance 152 can be predefined such that helical blades 122a, 122b follow a same helical path along pole 110 as would if helical blades 122a, 122b being parts of a single helical blade (e.g., helical blade 110, as shown in FIG. 6) in some embodiments, longitudinal distance 152 has a value of k pitches 159 where k is an integer (e.g., as shown in FIG. 6). In some embodiments, k is greater or equal to 2 (k≥2). Separation of helical blades 122a, 122b by longitudinal distance 152 can prevent continuous water flow along a whole length of pole 110 and provide at least two zones of target soil 80 (e.g., schematically separated by broken line 92 in FIG. 5E) through which water flow is discontinuous. In some embodiments, longitudinal distance 152 deviates by 2-4% from the value of k pitches 159 such that helical blade 122a) such that helical blade 122a, which can follow a screwing path of helical blade 122b during the screwing motion of the installation process, enters a undisturbed soil, thereby providing a good contact between helical blade 122a and/or RF electrodes 124a and a target soil, which does not follow a same screwing path of helical blade 122b during a screwing motion of an installation process, enters a undisturbed soil, thereby improving a contact between helical blade 122a and/or RF electrodes (e.g., RF electrodes 124-2a as shown in FIG. 5E) and target soil 80. These considerations may be applicable to any of the configurations of VWC sensors 100, including configurations with a central shaft (e.g., with pole 110). FIG. 6 further illustrates schematically that the distance between blades, indicated by 159a may correspond exactly or approximately to an integer number of pitches, represented schematically by the broken-line windings.

FIG. 6 is an illustration of configuration of volumetric water content (VWC) sensors 100a, 100b with a support 110 being a cureless helical blade, according to some embodiments of the invention. In some embodiments, coreless helical blade 110 has a tapered shape (e.g., as shown in FIG. 6). VWC sensors 100a, 100b can include at least one VWC probe 120, e.g., VWC probes 120a, 120b, as shown in FIG. 6. In some embodiments, VWC probes 120a, 120b are positioned concentrically along a longitudinal axis 155 of coreless helical blade 110 at predefined longitudinal locations and/or include RF electrodes 124a, 124b. In some embodiments, VWC probes 120a, 120b are VWC probes described in FIGS. 1-5. VWC sensors 100a, 100b can include at least one electronics unit (e.g., electronics unit 160 as shown in FIGS. 8-9). In some embodiments, the electronics units are embedded within careless helical blade 110 of VWC sensors 100a, 100b.

FIG. 7 is an illustration of a volumetric water content (VWC) probe 120 including segmented RF electrodes 124-3, according to some embodiments of the invention. FIG. 7 presents a top view of VWC, probe 120. In some embodiments, RF electrodes of VWC probe 120 (e.g., RF electrodes 124, 124-1, and/or 124-2 as shown in FIGS. 1-6) are segmented RF electrodes (e.g., RF electrodes 124-3, as shown in FIG. 7) that are secured and/or embedded within helical blade 122. In some embodiments, VWC probe 120 has eight pairs of segmented RF electrodes 124-3 (e.g., pairs 124-3a . . . 124-3g as shown in FIG. 7). In some embodiments, an RF field can be generated and/or measured by segmented RF electrodes 124-3 of each pair. RF fields measured by each pair of RF electrodes 124-3a . . . 124-3g can be averaged to determine a VWC of a target soil. In some embodiments, RF field measured by at least one pair of segmented RF electrodes, for example, by pair 123-3c, can significantly differs from RF fields measured by the rest of the pairs, for example due to accommodation of air bubbles on RF electrodes of pair 123-3c. Accordingly, RF field measured by pair 123-3c can be excluded from averaging, thereby eliminating introduction of measurement errors.

One advantage of the present invention can include enabling a self-tapping installation of VWC sensor 100. The self-tapping installation can include pushing tapered tip 112 of VWC sensor 100 into a target soil and/or establishing a rotational motion of the sensor about its longitudinal axis. The rotational motion of helical blades 122 secured along VWC sensor 100 (e.g., as shown in FIG. 1) can generate a screwing action that can wind the sensor into the target soil, such that no pre-drilling procedures are required, which minimizes the disturbance of the soil thereof and reduces vertical flow of water along pole 110 and/or helical blades 120.

During an installation of VWC sensor 100, a target soil can be disturbed in a vicinity of pole 110. Disclosed VWC sensor 100 can include RF electrodes 124 secured to helical blades 122 of VWC probes 120 at predefined radial distances from pole 110 (e.g., as shown in FIG. 1). Accordingly, another advantage of the present invention is that it can enable alienating the VWC measurement (e.g., by RF electrodes 124) away from pole 110 such that measurements of undisturbed soil are performed.

During an installation of VWC sensor 100, a target soil can also be disturbed in a vicinity of helical blades 122. Disclosed VWC sensor 100 can include RF electrode 124 secured to an outer lateral side of helical blade 122 and at least one RF electrode 124-2 embedded within the same helical blade 122 such that embedded RF electrodes 124-2 protrude above at least one of surfaces of the blade (e.g., as shown in FIGS. 5A-5B). Accordingly, another advantage of the present invention is that it can enable alienating the VWC measurement (e.g., by lateral RF electrodes 124 and protruding RF electrodes 124-2) away from the surfaces of helical blades 122 such that it can allow measurement of undisturbed soil.

FIG. 8 is a schematic block diagram illustrating an electronics unit 160 of volumetric water content (VWC) sensor 100, according to some embodiments of the invention in some embodiments, electronics unit 160 can be an enablement to a transmission line based on amplitude domain reflectometry (ADR), time domain reflectometry (TDR), frequency domain reflectometry (FDR) and/or time domain transmission (TDT) electronic circuits. Electronics unit 160 illustrated in FIGS. 7-8 is an enablement to a transmission line based on ADR electronic circuit as described below. In some embodiments, electronics unit 160 can be an enablement to a capacitance probe.

An RF signal can be generated by a source 161 (e.g., an oscillator). In some embodiments, the generated RF signal has a frequency of 100 MHz. The generated RF signal can be transmitted to a signal conditioning unit 162 (e.g., a filter to create a filtered RF signal. The filtered RF signal can be transmitted through a first transmission line 163 (e.g., phase shifter) and/or through a second transmission line 164 to a target soil. In some embodiments, at least a portion of transmission line 164 is at least one VWC probe 120 (e.g., as disclosed in FIG. 1, FIGS. 2A-2E, FIGS. 4A-4C and/or FIG. 5). In some embodiments, first transmission line 163 has an impedance value of $Z_L$ and/or second transmission line 164 has an impedance value of $Z_P$.

The impedance $Z_P$ of transmission line 164 can be based on a relative dielectric constant E of the target soil that surrounds transmission line 164. The relative dielectric constant E can be based on a moisture level of the target soil.

For example, Equation 1 shows the impedance $Z_P$ of the transmission 164 line as follows:

$$Z_P \propto \frac{1}{\sqrt{E}} \quad \text{(Equation 1)}$$

A reflection coefficient ρ of transmission line 163 and transmission line 164 can be based on $Z_L$, $Z_P$. For example, Equation 2 shows the reflection coefficient ρ as follows:

$$\rho = \frac{Z_P - Z_L}{Z_P + Z_L} \quad \text{(Equation 2)}$$

A voltage value $V_O$ (e.g., the filtered RF signal) at a junction 162a of filter 162 and transmission line 163 and/or a voltage value $V_P$ at a junction 163a of transmission line 163 and transmission line 164 can be based the reflection coefficient ρ. For example, Equation 3 and Equation 4 show the voltage value $V_O$ and the voltage value $V_P$ as follows:

$$V_O \propto (1-\rho) \quad \text{(Equation 3)}$$

$$V_P \propto (1+\rho) \quad \text{(Equation 4)}$$

The voltage value $V_O$ can also be based on forward voltage value $V_{FWD}$ and reflected voltage value $V_{REF}$. For example, Equation 5 shows the voltage value $V_O$ as follows:

$$V_O = V_{FWD} + V_{REF} \quad \text{(Equation 5)}$$

The voltage value $V_O$ and/or the voltage value $V_P$ can be measured by respective RF detectors 165, 166 and transmitted to a differential amplifier 167 to generate a differential voltage value $\Delta V = V_O V_P$. The differential voltage value $\Delta V$ can be based on the reflective coefficient ρ and as a result can be based on the dielectric constant ε of the moisture level of the target soil, such that allowing determining the value of ε. For example, Equation 6 shows the differential voltage value $\Delta V$ as follows:

$$\Delta V = V_O - V_P \propto 2\rho \propto \varepsilon \quad \text{(Equation 6)}$$

An example of a dependence of differential voltage value $\Delta V$ on the moisture level ε of the target soil is illustrated in graph 168.

FIG. 9 is a schematic block diagram of an electronic circuitry of electronics unit of volumetric water content (VWC) sensor 100, according to some embodiments of the invention. An oscillator 161 can generate a RF signal. The generated RF signal can be filtered by a filter 162 to generate a filtered RF signal. The filtered RF signal can be transmitted through a phase shifter 163 (e.g., that can act as a transmission line) and through a second transmission line 164 to a target soil.

Second transmission line 164 can include a switch 164-1 and/or a controller 164-2. Controller 164-2 can control switch 164-1 to connect phase shifter 163 to at least one of: a phase shifter 164-3a, a phase shifter 164-3b, a first reference load 164-4a and/or a second reference load 164-4b. In some embodiments, phase shifter 164-3a is connected to VWC probe 120a and/or phase shifter 164-3b is connected to VWC probe 120b, where VWC probes 120a, 120b can be VWC probes 120 disclosed in FIG. 1, FIGS. 2A-2E, FIGS. 4A-4C and/or FIG. 5. In some embodiments, VWC probes 120a, 120b are positioned at opposing ends along a longitudinal axis of VWC sensor 100, 100a.

A voltage value $V_O$ of the filtered RF signal can be measured by a peak detector 165 at a junction 162a of filter 162 and phase shifter 163 and/or a voltage value $V_P$ at a junction 163a of phase shifter 163 and transmission line 164 can be measured by a peak detector 166. The voltages values $V_O$ and $V_P$ can be transmitted to a differential amplifier 167 to generate a differential voltage value $\Delta V$. The voltage value $V_P$ and as a result differential voltage value $\Delta V$ can be a function of the level of moisture $\varepsilon$ of the target soil, as disclosed above (e.g., in Equations 1-6).

In some embodiments, phase shifters 164-3a, 163-3b rectify phase shifts that can be caused by a physical distance between junction 163a (where voltage value $V_P$ is measured) and VWC probes 120a, 120b. In some embodiments, reference loads 164-4a, 164-4b are used for a calibration of moisture sensor 100.

In some embodiments, the differential voltage value $\Delta V$ is digitalized by an analog to digital converter (ADC) 169 and/or transmitted to an external system 90 (e.g., cloud network).

Figure 10:
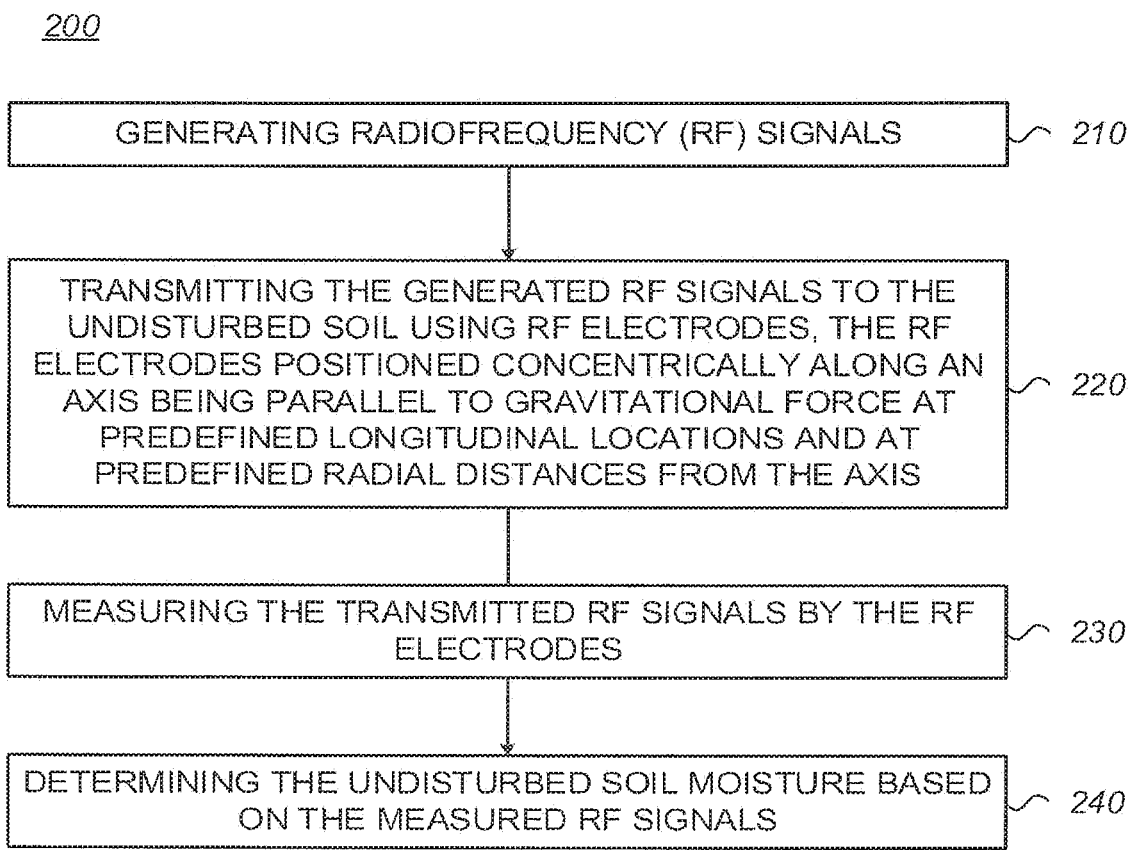
FIG. 10 is a flowchart illustrating a method of measuring a undisturbed volumetric water content (VCW), according to some embodiments of the invention.

FIG. 10 is a flowchart illustrating a method 200 of measuring a undisturbed volumetric water content (VWC), according to some embodiments of the invention. In some embodiments, method 200 can be carried out using VWC sensor 100 described above (e.g., as shown in FIGS. 1-7).

Method 200 can include generating 210 radiofrequency (RF) signals. Method 200 can include transmitting 220 the generated RF signals to the undisturbed soil using RF electrodes, the RF electrodes positioned concentrically along an axis being parallel to gravitational force at predefined longitudinal locations and at predefined radial distances from the axis.

In some embodiments, the RF electrodes have a helical shape. In some embodiments, the RF electrodes secured to helical blades, where the helical blades can be positioned concentrically along the axis at the predefined longitudinal locations. In some embodiments, the at least one of the RF electrodes is secured to an outer lateral side of the at least one of the helical blades. In some embodiments, the at least one of the RF electrodes is embedded within the at least one of the helical blades such that the at least one of the embedded RF electrodes protrudes above at least one of surfaces of that helical blade.

Method 200 can include measuring 230 the transmitted RF signals by the RF electrodes. Method 200 can include determining 240 the undisturbed VWC based on the measured RF signals.

FIG. 11 is a flowchart illustrating a method 300 of installing a soil sensor assembly, according to some embodiments of the invention. Method 300 can include providing 310 a soil sensor assembly including: a rotatably anchorable portion to be rotatably anchored in a soil; and at least one soil sensor mounted onto the rotatably anchorable portion. Method 300 can include rotatably inserting 320 the soil sensor assembly into a soil along an anchoring axis, thereby anchoring the soil moisture sensing assembly in the soil.

In some embodiments, the rotatably anchorable portion includes at least one threading arranged about the anchoring axis, the at least one threading includes at least one blade portion extending outwardly from the anchoring axis, wherein at least one moisture sensor is located on the at least one of the blade portions, and wherein the rotatably inserting of the soil sensor assembly into the soil along the anchoring axis, thereby anchoring the soil sensor assembly in the soil, is operative to bring the at least one moisture sensor located on the at least one of the blade portions into a soil moisture sensing engagement with a portion of the soil which is substantially undisturbed.

Figure 12A:
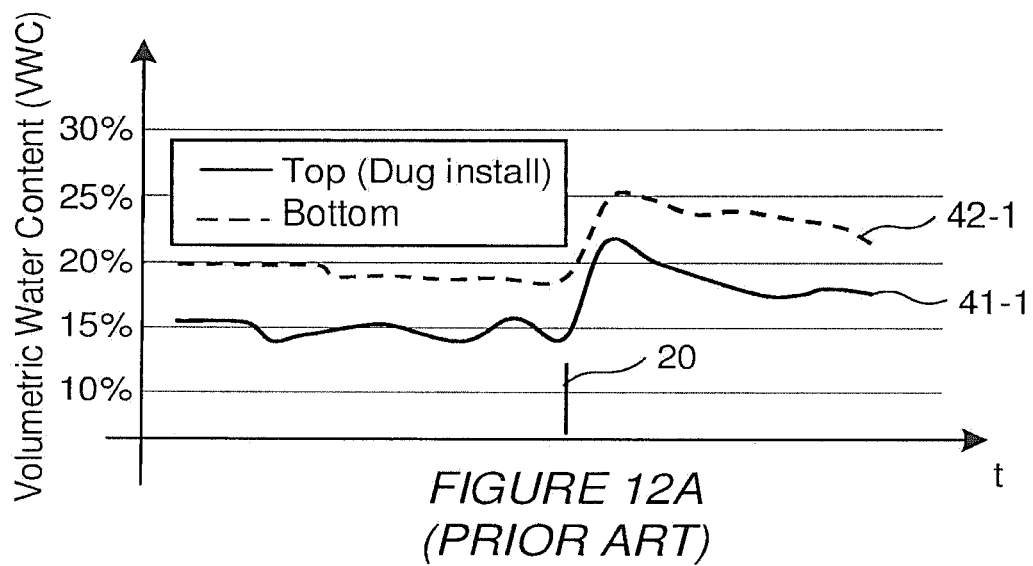
FIG. 12A is a graph illustrating volumetric water content (VWC) measurement results being measured by a prior art profile sensor, according to the prior art.
Figure 12B:
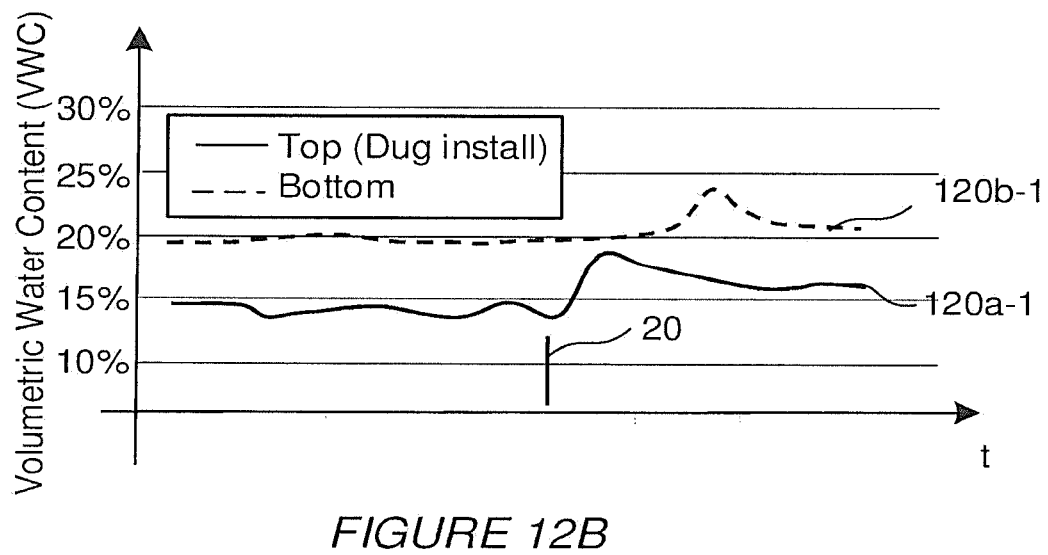
FIG. 12B is a graph illustrating volumetric water content (VWC) measurement results being measured by a VWC sensor, according to some embodiments of the invention.

FIG. 12A is a graph illustrating volumetric water content (VWC) measurement results being measured by a prior art profile sensor 40, according to the prior art. FIG. 12B is a graph illustrating volumetric water content (VWC) measurement results being measured by a VWC sensor 100, according to some embodiments of the invention.

Typically, following an irrigation event 20, measurements from bottom sensor 42 of prior art profile sensor 40 (e.g., as shown in FIG. 1A) can erroneously show a rise in VWC of a disturbed target soil (e.g., line 424 as shown in FIG. 12A) that can be similar in timing and amplitude, to measurements of top sensor 41 (e.g., line 41-1 as shown in FIG. 12A). Such measurements can be biased, since water takes time to filtrate down through undisturbed soil.

In contrast, the disclosed sensors were found to be sensitive and indicate irrigation events. Following an irrigation event 20, the VWC measurements generated by the VWC sensor 100 clearly show delay in timing between measurement of top sensor 120a (e.g., line 120a-1 as shown in FIG. 12B) and measurement of bottom sensor 120b (e.g., line 120b-1 as shown in FIG. 12B), which emphasizes that a target soil is undisturbed during an installation of VWC sensor 100.

In the following description, various aspects of the present invention are described. For purposes of explanation, specific configurations and details are set forth in order to provide a thorough understanding of the present invention. However, it will also be apparent to one skilled in the art that the present invention may be practiced without the specific details presented herein. Furthermore, well known features may have been omitted or simplified in order not to obscure the present invention. With specific reference to the drawings, it is stressed that the particulars shown are by way of example and for purposes of illustrative discussion of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before at least one embodiment of the invention is explained in detail, it is to be understood that the invention is not limited in its application to the details of construction and the arrangement of the components set forth in the following description or illustrated in the drawings. The invention is applicable to other embodiments that may be practiced or carried out in various ways as well as to combinations of the disclosed embodiments. Also, it is to be understood that the phraseology and terminology employed herein is for the purpose of description and should not be regarded as limiting.

Unless specifically stated otherwise, as apparent from the following discussions, it is appreciated that throughout the specification discussions utilizing terms such as "processing", "computing", "calculating" "determining", "enhancing" or the like, refer to the action and/or processes of a computer or computing system, or similar electronic computing device, that manipulates and/or transforms data represented as physical, such as electronic, quantities within the computing system's registers and/or memories into other data similarly represented as physical quantities within the computing system's memories, registers or other such information storage, transmission or display devices.

In the above description, an embodiment is an example or implementation of the invention. The various appearances of "one embodiment", "an embodiment", "certain embodiments" or "some embodiments" do not necessarily all refer to the same embodiments. Although various features of the invention may be described in the context of a single embodiment, the features may also be provided separately or in any suitable combination. Conversely, although the invention may be described herein in the context of separate embodiments for clarity, the invention may also be implemented in a single embodiment. Certain embodiments of the invention may include features from different embodiments disclosed above, and certain embodiments may incorporate elements from other embodiments disclosed above. The disclosure of elements of the invention in the context of a specific embodiment is not to be taken as limiting their use in the specific embodiment alone. Furthermore, it is to be understood that the invention can be carried out or practiced in various ways and that the invention can be implemented in certain embodiments other than the ones outlined in the description above.

The invention is not limited to those diagrams or to the corresponding descriptions. For example, flow need not move through each illustrated box or state, or in exactly the same order as illustrated and described. Meanings of technical and scientific terms used herein are to be commonly understood as by one of ordinary skill in the art to which the invention belongs, unless otherwise defined. While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

The invention claimed is:

1. A volumetric water content (VWC) sensor comprising:
    a support to enable installation of the VWC sensor in a target soil;
    one or more VWC probes positioned at a predefined longitudinal location along the support, each of the one or more VWC probes comprising:
        a helical blade secured along its inner lateral side to an outer surface of the support, and
        two or more radiofrequency (RF) electrodes secured to the helical blade at a predefined radial distance from the support; and
    one or more electronics units coupled to the two or more RF electrodes to transmit and receive RF signals from the two or more RF electrodes.

2. The VWC sensor of claim 1, wherein at least one of the two or more RF electrodes of the one or more VWC probes has a helical shape that corresponds to a shape of the helical blade of a corresponding one of the one or more VWC probes.

3. The VWC sensor of claim 1, wherein at least one of the two or more RF electrodes of the one or more VWC probes is secured to an outer lateral side of the helical blade of a corresponding one of the one or more VWC probes.

4. The VWC sensor of claim 3, wherein at least one of the two or more RF electrodes of the VWC probe is embedded within the helical blade of a corresponding one of the one or more VWC probes such that the at least one of the two or more RF electrodes protrudes above at least one surface of the helical blade.

5. The VWC sensor of claim 1, wherein at least one of the two or more RF electrodes of the one or more VWC probes is secured to at least one surface of the helical blade of a corresponding one of the one or more VWC probes.

6. The VWC sensor of claim 1, wherein at least one of the two or more RF electrodes of the one or move VWC probes is embedded within the helical blade of a corresponding one of the one or more VWC probes.

7. The VWC sensor of claim 1, wherein the support comprises a tip, wherein the tip comprises at least two prongs, and wherein each of the prongs comprises at least one further RF electrode.

8. The VWC sensor of claim 1, wherein at least one of the one or more electronics units is embedded within the helical blade of the at least one of the VWC probe a corresponding one of the one or more VWC probes.

9. The VWC sensor of claim 1, wherein at least one of the one or more VWC probes further comprises a protective layer configured to cover at least one of the two or more RF electrodes secured to the helical blade of the at least one of the one or more VWC probes.

10. The VWC sensor of claim 1, wherein each of the two or more RF electrodes is secured to the helical blade of a corresponding one of the VWC probes such that at least one of the two or more RF electrodes of a first one of the VWC probes faces at least one of the two or more RF electrodes of an adjacent second one of the VWC probes.

11. The VWC sensor of claim 1, wherein the helical blade of at least one of the one or more the VWC probes is at least one of the two or more RF electrodes.

12. A volumetric water content (VWC) sensor comprising:
    a VWC probe comprising two or more radiofrequency (RF) electrodes, wherein the VWC probe is configured to measure a VWC of a target soil in a measurement region between the two or more RF electrodes, and
    a support to secure positioning of the VWC probe, wherein the support occupies less than 10% of the measurement region, and wherein the support includes a helical blade,
    wherein the support is a pile and the VWC probe comprises a helical blade secured to the pile at a predefined longitudinal location, and
    wherein the at least two RF electrodes of the VWC probe are secured to the helical blade of the VWC probe.

13. The VWC sensor of claim 12, wherein at least one of the two or more RF electrodes of the VWC probe has a helical shape that corresponds to a shape of the helical blade of the VWC probe.

* * * * *